(12) United States Patent
Bai et al.

(10) Patent No.: US 8,221,634 B2
(45) Date of Patent: Jul. 17, 2012

(54) PROCESS AND APPARATUS FOR SEPARATING AND RECOVERING WASTE ALKALI FROM CYCLOHEXANE OXIDATION SOLUTION

(75) Inventors: Zhishan Bai, Shanghai (CN); Zhuoqun Qian, Shanghai (CN); Ji Ma, Shanghai (CN); Ping Zhou, Shanghai (CN); Yanhong Zhang, Shanghai (CN); Hualin Wang, Shanghai (CN)

(73) Assignee: East China University of Science and Technology, Shanghai (CN)

( * ) Notice: Subject to any disclaimer, the term of this patent is extended or adjusted under 35 U.S.C. 154(b) by 667 days.

(21) Appl. No.: 12/358,004

(22) Filed: Jan. 22, 2009

(65) Prior Publication Data

US 2010/0126938 A1    May 27, 2010

(30) Foreign Application Priority Data

Nov. 27, 2008    (CN) .......................... 2008 1 0203430

(51) Int. Cl.
*C07C 49/00* (2006.01)
*C07C 29/20* (2006.01)
*B01D 21/00* (2006.01)
*B01D 35/18* (2006.01)
*B01D 11/00* (2006.01)

(52) U.S. Cl. ........ 210/804; 568/375; 568/835; 585/802; 585/818; 585/833; 210/806; 210/788; 210/799; 210/800; 210/774; 210/634; 210/908

(58) Field of Classification Search .......... 210/804–806, 210/774, 634, 639, 702, 710, 712, 713, 737, 210/738, 749, 758, 765, 766, 767–770, 787–788, 210/800, 803, 511, 188, 195.1, 197, 205, 210/207, 208, 252, 259, 512.1, 512.2, 513, 210/532.1, 908, DIG. 5; 585/415, 802, 818, 585/833, 834; 568/342, 376, 835
See application file for complete search history.

(56) References Cited

U.S. PATENT DOCUMENTS 2,504,517 A * 4/1950 Greene ......................... 568/835
(Continued)

FOREIGN PATENT DOCUMENTS

CH            648542 A5 *   3/1985
(Continued)

OTHER PUBLICATIONS

Derwent WPI Acc No. 2008-L75086, English languge abstract for CN 101108794 (2008), pp. 1-7.*

(Continued)

*Primary Examiner* — Tony G Soohoo
*Assistant Examiner* — David C Mellon
(74) *Attorney, Agent, or Firm* — Hamre, Schumann, Mueller & Larson, P.C.

(57) ABSTRACT

A process and an apparatus for separating and recovering waste alkali from a cyclohexane oxidation solution are provided. A gradient combination of the gravity separation technique, the vortex separation technique and the coalescence separation technique is used to carry out fine separation of the waste alkali liquor from the cyclohexane oxidation solution. The purified cyclohexane oxidation solution is fed into a down-stream apparatus. Most of the waste alkali liquor thus separated is recycled, while the remaining is expelled. The expelled waste alkali liquor is incinerated in an incinerator, followed by recovering the molten species using a pneumatic pulverization process.

7 Claims, 1 Drawing Sheet

U.S. PATENT DOCUMENTS

| | | | | |
|---|---|---|---|---|
| 2,609,395 A | * | 9/1952 | Dougherty, Jr et al. | 568/342 |
| 2,931,834 A | * | 4/1960 | Crouch et al. | 568/357 |
| 3,275,692 A | * | 9/1966 | Waldmann et al. | 568/366 |
| 4,052,441 A | | 10/1977 | Brunner | |
| 4,163,027 A | * | 7/1979 | Magnussen et al. | 568/366 |
| 4,326,085 A | * | 4/1982 | De Cooker | 568/366 |
| 4,482,746 A | * | 11/1984 | Hermolin | 568/342 |
| 4,704,476 A | * | 11/1987 | Hartig et al. | 568/342 |
| 6,063,958 A | | 5/2000 | Chen et al. | |
| 6,340,420 B1 | * | 1/2002 | Dassel et al. | 204/529 |
| 2003/0045750 A1 | * | 3/2003 | Chou et al. | 562/524 |

FOREIGN PATENT DOCUMENTS

| | | | |
|---|---|---|---|
| CN | 101108794 B | * | 5/2010 |
| JP | 48042968 A | * | 2/1973 |

OTHER PUBLICATIONS

English language machine translation of CN 101108794 B, pp. 1-12.*

* cited by examiner

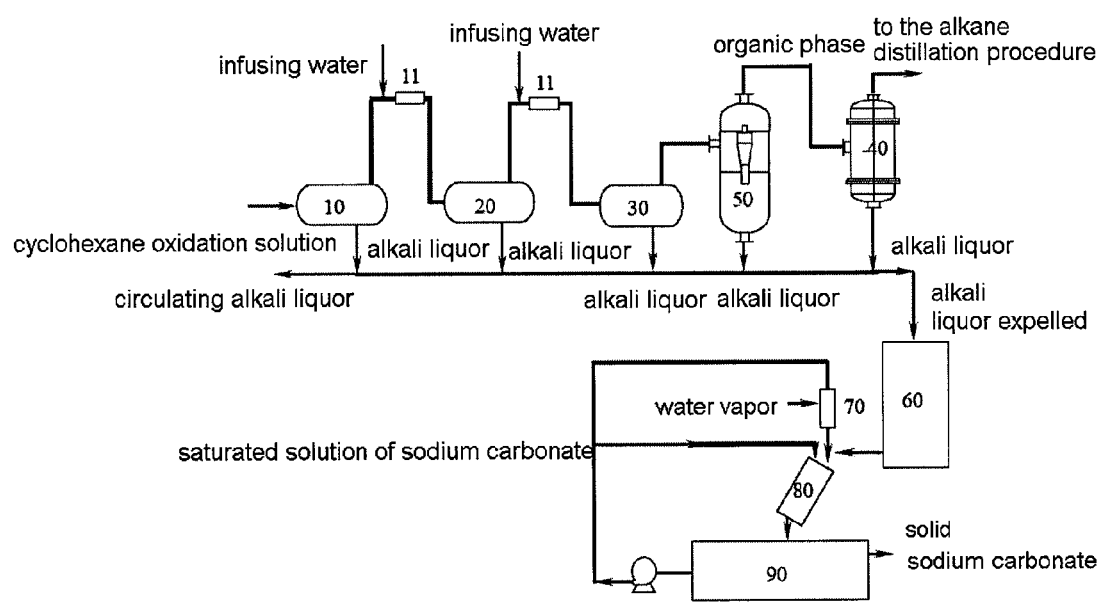

PROCESS AND APPARATUS FOR SEPARATING AND RECOVERING WASTE ALKALI FROM CYCLOHEXANE OXIDATION SOLUTION

CROSS-REFERENCE TO RELATED APPLICATIONS

This application claims priority to China Patent Application No. 200810203430.8, filed on Nov. 27, 2008, the entire contents of which are incorporated herein by reference.

FIELD OF THE INVENTION

The present invention relates to a new process for disposing waste alkali in a cyclohexane oxidation solution. In particular, the present invention relates to a process for separating and recovering the waste alkali from a cyclohexane oxidation solution. The process is effective in solving the problem that the waste alkali liquor in the feed of the alkane tower can not be separated completely, extending the length of the continuous operation cycle of the apparatus on a large scale, recovering molten species in solid state, and reducing discharge of pollutants, therefore suitable for separating and recovering waste alkali from chemical engineering apparatuses. The present invention also relates to an apparatus for separating and recovering the waste alkali from a cyclohexane oxidation solution.

BACKGROUND OF THE INVENTION

Primary processes for manufacturing cyclohexanone include hydrogenation of phenol, liquid-phase air oxidation of cyclohexane, hydration of cyclohexene, etc. Liquid-phase air oxidation of cyclohexane is the most widely used process in the world for manufacturing cyclohexanone and cyclohexanol due to its simple yet mature procedures and its necessity of relatively low one-time fixed investment. Currently 90% of the cyclohexanone in the world is produced by cyclohexane oxidation process.

Cyclohexane oxidation process for manufacturing cyclohexanone includes such procedures as oxidation, decomposition, saponification, waste alkali separation, alkane distillation, refining, dehydrogenation, heat recycling and tail gas reclamation. During the oxidation of cyclohexane, part of cyclohexane will be overoxidized to some neutral or acidic species which will further react with neutral alcohols to give esters. Thus, apart from the target product in the cyclohexane oxidation solution, there exist various acid byproducts and other complicated organic species with unidentified constituents. In order to separate these byproducts, crude oxidation products are generally disposed with aqueous solution of sodium hydroxide in a decomposition pot, so that the acids are neutralized and the esters are converted to sodium salts of organic acids and cyclohexanol by saponification. Following the reactions, the resulting cyclohexane oxidation solution is introduced into an alkali liquor separating system wherein the organic phase is separated from the alkali liquor. The organic phase separated out is directed to an alkane rectification procedure, and part of the alkali liquor is recycled with the rest expelled.

If the waste alkali liquor separating system of the cyclohexanone apparatus does not function well, waste alkali dispersed in the cyclohexane oxidation solution in minute form will render acyloin condensation in the reboiler of the alkane distillation tower, which will foul the reboiler and therefore deteriorate the effect of heat transfer so rapidly that the amount of evaporation is badly impaired till the reboiler can not operate properly. As a result, the whole apparatus has to stop work for the feed to be discharged and the reboiler to be cleaned. This will impact the operation cycle of the apparatus and increase the consumption of feedstock. The waste alkali liquor separated out, COD of which is up to several hundreds of thousands of mg/L, will bring about pollution to environment if it is drained off directly to the surroundings. Thus, efforts have been made to find technologies suitable for disposing the waste alkali liquor in a cyclohexane oxidation solution.

In the prior art, gravity sedimentation and coalescence separation are widely used in the waste alkali liquor separation procedure for the cyclohexanone apparatus to remove the waste alkali liquor. However, gravity sedimentation, when used to separate the waste alkali liquor from a cyclohexane oxidation solution, suffers from low efficiency of separation, long time of operation and dramatic expenditure on equipments. Moreover, only large particles (50 μm) can settle down effectively while fine particles can not. The object of complete separation of the fine particles can not be fulfilled merely by means of prolonging residence time in order to sedimentate them completely by gravity. A combination of gravity sedimentation and coalescence separation exhibits the advantage of high precision of separation with a cut diameter up to 0.1 μm, but it has the drawbacks that the coalescence elements are readily blocked when the solution is not clean, the anti-shock capability of the apparatus is low, the apparatus will lose ability of separation when there is a relatively heavy amount of waste alkali liquor, and the coalescence elements needs frequent replacement which leads to high operational cost.

The major portion of the waste alkali liquor separated from the waste alkali liquor separation system of the cyclohexanone apparatus is recycled, while the rest is expelled from the apparatus. In the prior art, the waste alkali liquor expelled from the apparatus is generally disposed by neutralization with acid and/or by incineration.

In a process disclosed by U.S. Pat. No. 4,052,441, the waste alkali liquor separated from the cyclohexane oxidation solution was neutralized by adding sulfuric acid, and an oil phase and a water phase were obtained after separation, wherein the water phase was an aqueous solution of sodium sulfate and the oil phase comprised organic acids; after removing the low-boiling-point monobasic acids and water by vacuum distillation, the oil phase was cooled and crystallized to recover adipic acid; then the mother liquor obtained was redistilled to recover monobasic acids, dibasic acids, etc., and then esterized to obtain ester products. In a process disclosed by U.S. Pat. No. 6,063,958, the waste alkali liquor was neutralized using an inorganic protonic acid, and an oil phase and a water phase were obtained after separation, wherein the water phase was an aqueous solution of an inorganic salt and the oil phase was extracted using an aqueous solution of an inorganic protonic acid to obtain adipic acid and 6-hydroxyl caproic acid at a total yield of 50-55%. Although many useful substances can be recovered from the waste alkali liquor by means of neutralization with an acid, the process suffers from complicated procedures, poor purity of the recovered organic acids and low total recovery efficiency. Furthermore, a lot of organic residues remain in water which has a COD of over one hundred of thousands of mg/L, and thus needing to be incinerated or disposed otherwise.

Incineration used to dispose the waste alkali liquor can eliminate organic species, but inorganic species (e.g. bases) are left over. Following incineration, part of the sodium carbonate is introduced into a flue along with smoke, and then recovered by electrostatic adsorption. The molten sodium carbonate at the bottom of the incinerator chamber is dissolved in water and then drained off. Notwithstanding the very low COD of the aqueous solution of sodium carbonate, the result of incineration is nothing more than a conversion from a heavy pollution to a light one.

So far, the technologies for disposing the waste alkali liquor in the cyclohexanone apparatus in the prior art have never met the demand of fine separation, neither have they tackled the problem of environmental pollution. Thus, an urgent need exists for the development of a new technology suitable for disposing the waste alkali liquor in a cyclohexane oxidation solution in a long operation cycle.

SUMMARY OF INVENTION

According to the present invention, a gradient combination of vortex-coalescence is applied to separate the waste alkali liquor from a cyclohexane oxidation solution, so as to provide an effective solution to the problem of incomplete separation of the waste alkali liquor from the cyclohexane oxidation apparatus and to extend the effective production time of the alkane distillation tower considerably; and such processes as incineration and spray granulation are used to dispose the waste alkali liquor thus separated, so as to solve the problem of environmental pollution and recover solid sodium carbonate. Therefore, the problems in the prior art have been solved.

In one aspect of the invention, a process is provided for separating and recovering the waste alkali liquor from a cyclohexane oxidation solution, comprising:

(a) sedimentating by gravity the cyclohexane oxidation solution into which a solution of sodium hydroxide has been added, giving a mixture of the first separation step, i.e. a cyclohexane oxidation solution removed of over 99% alkali liquor;

(b) washing the mixture of the first separation step with water, so that the alkaline species in the feedstock migrate to water and the alkaline species in water are enriched, wherein the resulting mixture of the mixture of the first separation step and water which are mixed thoroughly is subjected to gravity sedimentation to obtain a mixture of the second separation step, i.e. a cyclohexane oxidation solution further removed of 95%-99% alkali liquor;

(c) washing the mixture of the second separation step with water, wherein the resulting mixture of the mixture of the second separation step and water which are mixed thoroughly is subjected to gravity sedimentation to obtain a mixture of the third separation step, i.e. a cyclohexane oxidation solution further removed of 95%-99% alkali liquor;

(d) vortex-separating the mixture of the third separation step at a temperature in the range of 50-200° C. and a pressure drop in the range of 0.1-0.25 MPa to further remove the alkali liquor comprising alkaline species, giving a mixture of the fourth separation step, i.e. a cyclohexane oxidation solution further removed of 85%-98% alkali liquor;

(e) coalescence-separating the mixture of the fourth separation step at a temperature in the range of 50-200° C. and a pressure drop in the range of 0.05-0.15 MPa to further remove the alkali liquor comprising alkaline species, giving a cyclohexane oxidation solution comprising less than 3 mg/L $Na^+$ that is left over;

(f) recycling 80%-90% of the waste alkali liquor separated by the above combination of gravity sedimentation-vortex separation-coalescence separation, with the remaining 10%-20% expelled;

(g) subjecting the 10%-20% of the waste alkali liquor expelled to incineration in an incinerator, wherein part of the resulting sodium carbonate after incineration is introduced into a flue along with smoke and recovered by electrostatic adsorption, while the molten sodium carbonate flows out from the bottom of the incinerator chamber;

(h) setting a guide bucket underneath the outlet of the incinerator for the molten effluent to flow out, wherein a saturated solution of the effluent, which will be recycled, is kept spurting in the guide bucket, and the molten effluent is crushed by a gas-water mixture from a spurting nozzle before it drops into the effluent solution; and (i) subjecting the saturated solution of the effluent comprising solids to solid-liquid separation, after which the solid particles are dried and packaged, while the saturated solution of the effluent is pressurized and then recycled into the guide bucket.

In one preferred embodiment, the water content of the cyclohexane oxidation solution after mixing thoroughly with water in step (b) is 0.5%-0.8% by volume.

In another preferred embodiment, the second separation step is carried out at a temperature of 60-130° C. and a pressure drop of 0.15 MPa.

In another preferred embodiment, the third separation step is carried out at a temperature of 60-90° C. and a pressure drop of 0.08 MPa.

In another preferred embodiment, the third separation step is carried out with a gravity sedimentation tank.

In another aspect of the invention, an apparatus for separating and recovering the waste alkali liquor from a cyclohexane oxidation solution is provided, comprising:

A saponification separator, used for sedimentating by gravity the cyclohexane oxidation solution into which a solution of sodium hydroxide has been added, giving a mixture of the first separation step, i.e. a cyclohexane oxidation solution removed of over 99% alkali liquor;

A mixer connected to the saponification separator, used for infusing water into the mixture of the first separation step and mixing thoroughly the mixture of the first separation step with water;

A first water-washing separator connected to the mixer, used for washing the mixture of the first separation step with water, so that the alkaline species in the feedstock migrate to water and the alkaline species in water are enriched, wherein the resulting mixture of the mixture of the first separation step and water which are mixed thoroughly is subjected to gravity sedimentation to obtain a mixture of the second separation step, i.e. a cyclohexane oxidation solution further removed of 95%-99% alkali liquor;

A mixer connected to the first water-washing separator, used for infusing water into the mixture of the second separation step and mixing thoroughly the mixture of the second separation step with water;

A second water-washing separator connected to the mixer, used for washing the mixture of the second separation step with water, wherein the resulting mixture of the mixture of the second separation step and water which are mixed thoroughly is subjected to gravity sedimentation to obtain a mixture of the third separation step, i.e. a cyclohexane oxidation solution further removed of 95%-99% alkali liquor;

A vortex separator connected to the second water-washing separator, used for vortex-separating the mixture of the third separation step at a temperature in the range of 50-200° C. and a pressure drop in the range of 0.1-0.25 MPa to further remove alkali liquor comprising alkaline species, giving a mixture of the fourth separation step, i.e. a cyclohexane oxidation solution further removed of 85%-98% alkali liquor; the vortex separator comprising a tank body, an inlet for supplying the cyclohexane oxidation solution further removed of 95%-99% alkali liquor from the second water-washing separator, an outlet for discharging the alkali liquor comprising alkaline species, and an outlet for discharging the cyclohexane oxidation solution further removed of 85%-98% alkali liquor, wherein the inlet for supplying the cyclohexane oxidation solution further removed of 95%-99% alkali liquor from the second water-washing separator and the outlet of the second water-washing separator for discharging the cyclohexane oxidation solution further removed of 95%-99% alkali liquor are connected via a pipe;

A coalescence separator connected to the vortex separator, used for coalescence-separating the mixture of the fourth separation step at a temperature in the range of 50-200° C. and a pressure drop in the range of 0.05-0.15 MPa to further remove the alkali liquor comprising alkaline species, giving a cyclohexane oxidation solution comprising less than 3 mg/L $Na^+$ that is left over; the coalescence separator comprising a tank body, an inlet for supplying the cyclohexane oxidation solution removed of 85%-98% alkali liquor from the vortex separator, an outlet for discharging the alkali liquor comprising alkaline species, and an outlet for discharging the cyclohexane oxidation solution comprising less than 3 mg/L $Na^+$ that is left over, wherein the inlet for supplying the cyclohexane oxidation solution further removed of 85%-98% alkali liquor from the vortex separator and the outlet of the vortex separator for discharging the cyclohexane oxidation solution further removed of 85%-98% alkali liquor are connected via a pipe;

An incinerator disposed underneath the saponification separator, the first water-washing separator, the second water-washing separator, the vortex separator and the coalescence separator, for incinerating the waste alkali liquor expelled;

A guide bucket disposed underneath the outlet of the incinerator for the molten effluent to flow out, used for keeping a saturated solution of the effluent spurting and for recycling the saturated solution of the effluent;

A spurting nozzle for a gas-water mixture disposed underneath the outlet of the incinerator for the molten effluent to flow out, used for crushing the molten effluent; and A solid-liquid separator connected to the guide bucket in circulation, used for subjecting the saturated solution of the effluent comprising solids to solid-liquid separation, wherein the second water-washing separator carries out the process of separation via a gravity sedimentation tank which comprises a tank body, an inlet for supplying the waste alkali feedstock derived from the cyclohexane oxidation solution, an outlet for discharging the alkali liquor comprising alkaline species, and an outlet for discharging the cyclohexane oxidation solution removed of 95%-99% alkali liquor.

In one preferred embodiment, the water phase flux in the vortex separator is 1%-5% that of its entrance flux.

In another preferred embodiment, the second water-washing separator takes the form of single stage or multi-stage in tandem.

In another preferred embodiment, the vortex separator takes the form of single stage or multi-stage in tandem.

In another preferred embodiment, the coalescence separator takes in the form of single stage or multi-stage in tandem.

DESCRIPTION OF THE DRAWINGS

FIG. 1 shows the schematic flow chart of the process for disposing the waste alkali liquor in accordance with the invention.

DETAILED DESCRIPTION OF INVENTION

After extensive and intensive study, the present inventors have found that, when a gradient combination of a gravity sedimentation tank, a vertex separator and a coalescence separator is used to separate the waste alkali liquor from a cyclohexane oxidation solution, the problem of incomplete separation of the waste alkali liquor from the cyclohexane oxidation apparatus in the prior art can be effectively solved, such drawbacks as the non-ideal effect existing in the gravity sedimentation method and the frequent washing needed by the coalescence separation method can be overcome, and the effective production time of the alkane distillation tower can be extended considerably. Furthermore, when incineration and spray granulation are used to dispose the waste alkali liquor thus separated, the problem of environmental pollution can be solved, and solid sodium carbonate can be recovered. Based on the foregoing findings, the present invention is achieved.

The technical idea on separating the waste alkali liquor in accordance with the invention is the use of a gradient combined separation process to dispose the waste alkali liquor in the cyclohexane oxidation solution. The separation precision of a vortex separator (which has a cut diameter of 10 μm and can be used to dispose a cyclohexane oxidation solution comprising 0.1%-30% alkali liquor, so that it is substantially flexible in operation) is higher than that of a gravity sedimentation tank, and the separation precision of a coalescence separator (which has a cut diameter of 0.1 μm but can not be used to dispose a cyclohexane oxidation solution comprising too much alkali liquor, for the separation efficiency will decrease due to the incapability of the particles in the alkali liquor to coalesce in time when the content of the alkali liquor is too high, even if a gravity sedimentation tank is combined with a coalescence separator in tandem to remove the alkali liquor from the cyclohexane oxidation solution, as evidenced by the industrial practice which shows that the content of the alkali liquor in the cyclohexane oxidation solution at the outlet of the gravity sedimentation tank, or the inlet of the coalescence separator, is still detrimentally high for the separation of the coalescence separator) is higher than that of a vortex separator. Thus, if a single stage separator or multi-stage vertex separators are disposed between the gravity sedimentation tank and the coalescence separator, the content of the alkali liquor in the cyclohexane oxidation solution at the inlet of the coalescence separator can be decreased to a degree sufficient to enhance the disposal effect of the coalescence separator significantly, resulting in the decrease of the content of the alkali liquor in the cyclohexane oxidation solution at the outlet of the coalescence separator. With full account of the characteristics of the gravity sedimentation tank, the vortex separator and the coalescence separator being taken in accordance with the invention, the alkali liquor is separated from a cyclohexane oxidation solution using a gravity sedimentation tank at a first step; then, a second separation step is carried out by disposing particles of diameter larger than 10 μm in the alkali liquor using a vortex separator; and at last, a coalescence separator is used to dispose particles of diameter smaller than 10 μm at a lower content in the alkali liquor as a third step. Therefore, the above three kinds of equipments are combined effectively in a gradient separation mode to dispose the alkali liquor in a cyclohexane oxidation solution and the separation efficiency is enhanced.

The technical idea on recovering the effluent from an incinerator in which 10%-20% of the waste alkali liquor expelled is incinerated is based on the following considerations. In the course of incineration, the molten species is characterized by great variation in flux, temperature and flowability. When the temperature of the molten species is over 880° C., even up to 1000° C., the molten species is highly corrosive. Water will be vaporized immediately when it gets into contact with the molten species and the volume of the vapor expands abruptly. This will readily lead to explosion. Thus, molten sodium carbonate can not be recovered successfully unless the problems that the molten species is broken, cooled and transferred before it gets into contact with the surface of other objects can be solved. On the basis of the characteristics of the molten species and the aqueous solution of sodium carbonate, the inventors have designed a scheme to pulverize the molten species in virtue of the spurting force of a gas-liquid mixture and carry it in a solution. Specifically, water vapor and a saturated solution of sodium carbonate pressurized by a circulating pump are used as a medium to spurt on the molten species. After the crushed melt stream gets into the saturated solution of sodium carbonate, a circulating stream of the saturated solution of sodium carbonate is arranged, based on the principle that no more solute can be dissolved in its saturated solution, to carry the particles of sodium carbonate at high temperature into a solid-liquid separating unit to achieve solid-liquid separation. After solid-liquid separation, the cooled particles of sodium carbonate are sent out by a carrying unit and recovered.

In a first aspect of the invention, a process is provided for disposing the waste alkali liquor in a cyclohexane oxidation solution, comprising:

(a) sending the cyclohexane oxidation solution, into which a solution of sodium hydroxide has been added, into a saponification separator for gravity sedimentation, resulting in a mixture of the first separation step, i.e. a cyclohexane oxidation solution removed of over 99% alkali liquor;

(b) washing the mixture of the first separation step with water, so that the alkaline species in the feedstock migrate to water and the alkaline species in water are enriched, wherein the resulting mixture of the mixture of the first separation step and water which are mixed thoroughly in a mixer is fed into the first water-washing separator for gravity sedimentation, resulting in a mixture of the second separation step, i.e. a cyclohexane oxidation solution further removed of 95%-99% alkali liquor;

(c) washing the mixture of the second separation step with water, wherein the resulting mixture of the mixture of the second separation step and water which are mixed thoroughly in a mixer is fed into the second water-washing separator for gravity sedimentation, resulting in a mixture of the third separation step, i.e. a cyclohexane oxidation solution further removed of 95%-99% alkali liquor;

(d) vortex-separating the mixture of the third separation step at a temperature in the range of 50-200° C. and a pressure drop in the range of 0.1-0.25 MPa to further remove the alkali liquor comprising alkaline species, giving a mixture of the fourth separation step, i.e. a cyclohexane oxidation solution further removed of 85%-98% alkali liquor;

(e) coalescence-separating the mixture of the fourth separation step at a temperature in the range of 50-200° C. and a pressure drop in the range of 0.05-0.15 MPa to further remove the alkali liquor comprising alkaline species, giving a downstream equipment a cyclohexane oxidation solution comprising less than 3 mg/L $Na^+$ that is left over;

(f) recycling 80%-90% of the waste alkali liquor separated by the combination of gravity sedimentation-vortex separation-coalescence separation, with the remaining 10%-20% expelled;

(g) subjecting 10%-20% of the waste alkali liquor expelled to incineration in an incinerator, wherein part of the resulting sodium carbonate after incineration is introduced into a flue along with smoke and recovered by electrostatic adsorption, while the molten sodium carbonate flows out from the bottom of the incinerator chamber;

(h) setting a guide bucket underneath the outlet of the incinerator for the molten effluent to flow out, wherein a saturated solution of the effluent, which will be recycled, is kept spurting in the guide bucket, and the molten effluent is crushed by a gas-water mixture from a spurting nozzle before it drops into the effluent solution; and (i) subjecting the saturated solution of the effluent comprising solids to solid-liquid separation, after which the solid particles are dried and packaged, while the saturated solution of the effluent is pressurized by a pump and then recycled into the guide bucket.

Preferably, in step (b), the water content of the cyclohexane oxidation solution after infusing water is 0.5%-0.8% by volume.

Preferably, in step (c), the second separation step is carried out at a temperature of 60-130° C. and a pressure drop of 0.15 MPa.

Preferably, in step (d), the third separation step is carried out at a temperature of 60-90° C. and a pressure drop of 0.08 MPa.

In a second aspect of the invention, an apparatus for disposing the waste alkali liquor in a cyclohexane oxidation solution is provided, comprising:

A gravity sedimentation tank, used for removing the alkali liquor comprising alkaline species in the waste alkali feedstock derived from a cyclohexane oxidation solution, so as to give a cyclohexane oxidation solution removed of 95%-99% alkali liquor; the gravity sedimentation tank comprising a tank body, an inlet for supplying the waste alkali feedstock derived from the cyclohexane oxidation solution, an outlet for discharging the alkali liquor comprising alkaline species, and an outlet for discharging the cyclohexane oxidation solution removed of 95%-99% alkali liquor;

A vortex separator, used for further removing the alkali liquor comprising alkaline species in the waste alkali feedstock derived from the cyclohexane oxidation solution, so as to give a cyclohexane oxidation solution further removed of 85%-98% alkali liquor; the vortex separator comprising a tank body, an inlet for supplying the cyclohexane oxidation solution further removed of 95%-99% alkali liquor from the gravity sedimentation tank, an outlet for discharging the alkali liquor comprising alkaline species, and an outlet for discharging the cyclohexane oxidation solution further removed of 85%-98% alkali liquor, wherein the inlet for supplying the cyclohexane oxidation solution further removed of 95%-99% alkali liquor from the gravity sedimentation tank and the outlet of the gravity sedimentation tank for discharging the cyclohexane oxidation solution further removed of 95%-99% alkali liquor are connected via a pipe;

A coalescence separator, used for further removing the alkali liquor comprising alkaline species in the waste alkali feedstock derived from the cyclohexane oxidation solution, so as to give a cyclohexane oxidation solution comprising less than 3 mg/L $Na^+$ that is left over; the coalescence separator comprising a tank body, an inlet for supplying the cyclohexane oxidation solution removed of 85%-98% alkali liquor from the vortex separator, an outlet for discharging the alkali liquor comprising alkaline species, and an outlet for discharging the cyclohexane oxidation solution comprising less than 3 mg/L $Na^+$ that is left over, wherein the inlet for supplying the cyclohexane oxidation solution further removed of 85%-98% alkali liquor from the vortex separator and the outlet of the vortex separator for discharging the cyclohexane oxidation solution further removed of 85%-98% alkali liquor are connected via a pipe;

An incinerator, used for converting the waste alkali liquor into molten sodium carbonate through incineration;

A spurting nozzle for a gas-water mixture, used for forming a spurting stream of the gas-water mixture, and crushing and preliminarily cooling the molten effluent; and A solid-liquid separator, used for separating the solid particles from the saturated solution of the effluent comprising solids, wherein the saturated solution is pressurized by a pump and returned to the guided bucket.

Preferably, the apparatus further comprises a water-washing separator connected to the outlet of the gravity sedimentation tank for supplying the waste alkali feedstock derived from the cyclohexane oxidation solution via a pipe, and a saponification separator connected to the water-washing separator via a pipe.

Preferably, the water phase flux in the vortex separator is 1%-5% that of its entrance flux.

Preferably, the vortex tubes of the vortex separator may share a feeding chamber, an oil-phase exit chamber and an oil-containing sewage exit chamber. The feeding chamber and the exit chambers may be three separate vessels, or they may be three parts of one single vessel for the configuration of the apparatus to be simplified.

The vortex separator used in the invention can be any one of the various conventional vortex separators in the art, which may take the form of single stage or multi-stage.

There is no specific limitation on the gravity sedimentation tank used in the invention. It can be any one of the various conventional gravity sedimentation tanks in the art for separating the waste alkali liquor from a cyclohexane oxidation solution. The gravity sedimentation tank may take the form of single stage or multi-stage, though that of three-stage in tandem is usually used.

There is no specific limitation on the coalescence separator used in the invention, either. It can be any one of the various conventional coalescence separators in the art for separating the waste alkali liquor from a cyclohexane oxidation solution. The coalescence separator may take the form of single stage or multi-stage.

There is no specific limitation on the incinerator used in the invention, either. It can be any one of the various conventional incinerators in the art for incinerating the waste alkali.

There is no specific limitation on the spurting nozzle for a gas-water mixture used in the invention, either. It can be any one of the various conventional spurting nozzles for a gas-water mixture.

There is no specific limitation on the solid-liquid separator used in the invention, either. It can be any one of the various conventional solid-liquid separators.

Now turn to the drawing.

FIG. 1 shows the process for disposing waste alkali liquor in accordance with one embodiment of the invention. As shown in FIG. 1, the process for disposing waste alkali liquor concerns two parts, i.e. a system for separating the waste alkali liquor and a system for disposing the waste alkali liquor separated. First, a cyclohexane oxidation solution into which a solution of sodium hydroxide has been added is fed into a saponification separator 10 to carry out the saponification separation. And then, the mixture thus separated is washed with water, so that the alkaline species in the feedstock migrate to water and the alkaline species in water are enriched. The resulting mixture is mixed thoroughly with water in a mixer 11, and then fed into the first water-washing separator 20 for gravity sedimentation, giving a mixture of the second separation step, i.e. a cyclohexane oxidation solution removed of 95%-99% alkali liquor. The mixture of the second separation step is washed with water before it is mixed thoroughly with water in the mixer 11 and fed into the second water-washing separator 30 for gravity sedimentation, giving a mixture of the third separation step, i.e. a cyclohexane oxidation solution removed of 95%-99% alkali liquor. The mixture of the third separation step is then fed into a vertex separator 50 where the vortex separation is carried out at a temperature in the range of 50-200° C. and a pressure drop in the range of 0.1-0.25 MPa to further remove the alkali liquor comprising alkaline species, giving a mixture of the fourth separation step, i.e. a cyclohexane oxidation solution further removed of 85%-98% alkali liquor. Subsequently, the mixture of the fourth separation step is fed into a coalescence separator 40 where the coalescence separation is carried out at a temperature in the range of 50-200° C. and a pressure drop in the range of 0.05-0.15 MPa to further remove the alkali liquor comprising alkaline species, giving a cyclohexane oxidation solution comprising less than 3 mg/L $Na^+$ that is left over, i.e. a purified cyclohexane oxidation solution. The purified cyclohexane oxidation solution may be fed into a downstream equipment such as an alkane distillation tower for further processing. Of the waste alkali liquor separated by a combinatorial technique of gravity sedimentation-vortex separation-coalescence separation, 80%-90% is recycled, while 10%-20% is expelled. The expelled waste alkali liquor is fed into an incinerator 60 for incineration. After incineration, part of the resulting sodium carbonate is discharged into a flue along with smoke and recovered by electrostatic adsorption. Molten sodium carbonate flows out of the incinerator from its bottom. A guide bucket 80 is disposed underneath the outlet of the incinerator for the molten effluent, where a saturated solution of the effluent is kept spurting uninterruptedly in the guide bucket, and the saturated solution is recycled. The molten effluent is crushed by a gas-water mixture from a spurting nozzle 70 before it drops into the effluent solution. The saturated solution of the effluent comprising solids is fed into a solid-liquid separator 90 for solid-liquid separation. The solid particles thus separated are dried and packaged, while the saturated solution is pressurized by a pump and then recycled into the guide bucket 80.

The primary advantages of the invention are as follow:

(i) A gradient combination of the vertex separation technique and the coalescence separation technique takes full advantages of the vertex separation excelling at coarse separation and the coalescence separation excelling at fine separation. This strategy of gradient separation overcomes the defects in the prior art that the separating apparatus costs high in operation and the separation effect is not satisfactory. Furthermore, the operation cycle of the apparatus is prolonged on a large scale;

(ii) The incineration-spurting process used to dispose the waste alkali liquor substantially eliminates drainage of waste alkali liquor and COD, so that a good effect of environmental protection is achieved. A crude product of sodium carbonate can be recovered from the effluent, which exhibits the nice economic effect of the process;

(iii) The apparatus of the invention is easy to be put into practice due to its simple configuration. It is convenient in manipulation and suitable for long-cycle operation.

While it is well suited to separate the waste alkali liquor from a cyclohexane oxidation solution, it may be adapted to other chemical engineering systems for separating waste alkali liquor.

EXAMPLES

The invention will be explained in more detail with reference to specific examples. However, it is to be understood that these examples are only used to clarify the invention, without any intention to limit the scope of the invention. In the following examples, if no conditions are denoted for any given testing process, in general, either conventional conditions or conditions advised by manufacturers should be followed. Unless otherwise noted, all percentages and parts are based on weight.

Process for Separating the Waste Alkali Liquor from a Cyclohexane Oxidation Solution The process for separating the waste alkali liquor from a cyclohexane oxidation solution is shown in FIG. 1.

1. Properties of the Feed

The feed is a mixture of an organic phase and an inorganic phase.
Rated flux: 275 ton/hour;
Temperature: 95-115° C., about 105° C. on average;
Density: 856.4 kg/m$^3$ for the organic phase; 954.7 kg/m$^3$ for the inorganic phase calculated as water at 105° C.
Viscosity: $0.665 \times 10^{-3}$ Pa·s for the organic phase.

2. Content Determination

The content of Na$^+$ is determined using atomic adsorption spectrophotometry;
The content of water is determined using chromatography.

3. Effect of the Process (1) The content of Na$^+$ in the feed of the alkane tower is lowered from 50-100 mg/L to less than 3 mg/L. The operation cycle of the alkane tower is prolonged from 1-2 months to more than 7 months, which means that the continuous operation time of the alkane distillation tower is extended in a large scale. The consumption of feed is reduced, wherein less than 1000 kg/ton of benzene is consumed.

(2) The yield of cyclohexanone is promoted, owing to the decrease of alkali content in the feed of the alkane tower.

(3) COD of the expelled effluent is substantially zero. Waste alkali liquor expelled is reduced by 60000 ton/year, and 6000 tons of solid sodium carbonate is recovered per year.

All references mentioned in the specification are incorporated herein by reference, as if each of them sets forth independently. Moreover, it is to be understood that many variations or modifications of the invention may be made by those skilled in the art after reading the foregoing teachings, and these equivalents will fall in the scope defined by the appended claims of the application.

What is claimed is:

1. A process for separating and recovering waste alkali from a cyclohexane oxidation solution, comprising the following steps:
(a) a first separation step that comprises sedimentating by gravity a cyclohexane oxidation solution that contains a solution of sodium hydroxide, giving a mixture of the first separation step that includes a cyclohexane oxidation solution removed of over 99% alkali liquor;
(b) a second separation step that comprises washing the mixture of the first separation step with water, so that the alkaline species in the feedstock migrate to water and the alkaline species in water are enriched, wherein the resulting mixture of the mixture of the first separation step and water which are mixed thoroughly is subjected to gravity sedimentation to obtain a mixture of the second separation step that includes a cyclohexane oxidation solution further removed of 95%-99% alkali liquor;
(c) a third separation step that comprises washing the mixture of the second separation step with water, wherein the resulting mixture of the mixture of the second separation step and water which are mixed thoroughly is subjected to gravity sedimentation to obtain a mixture of the third separation step that includes a cyclohexane oxidation solution further removed of 95%-99% alkali liquor;
(d) a fourth separation step that comprises vortex-separating the mixture of the third separation step at a temperature in the range of 50-200° C. and a pressure drop in the range of 0.1-0.25 MPa to further remove alkali liquor comprising alkaline species, giving a mixture of the fourth separation step that includes a cyclohexane oxidation solution further removed of 85%-98% alkali liquor;
(e) coalescence-separating the mixture of the fourth separation step at a temperature in the range of 50-200° C. and a pressure drop in the range of 0.05-0.15 MPa to further remove alkali liquor comprising alkaline species, giving a cyclohexane oxidation solution comprising less than 3 mg/L Na$^+$ that is left over;
(f) recycling 80%-90% of the alkali liquor removed by the steps (a), (b), (c), (d) and (e) to be mixed with the cyclohexane oxidation solution in the step (a) with the remaining 10%-20% expelled;
(g) subjecting the remaining 10%-20% of the alkali liquor expelled to incineration in an incinerator to obtain a molten effluent including sodium carbonate, the molten effluent flowing out from the bottom of an incinerator chamber;
(h) setting a guide bucket underneath an outlet of the incinerator chamber for the molten effluent to flow out, wherein a saturated solution of sodium carbonate is spurting in the guide bucket, and the molten effluent is crushed by a gas-water mixture from a spurting nozzle before the molten effluent drops into the guide bucket to form a saturated effluent solution; and
(i) subjecting the saturated effluent solution comprising solids to a solid-liquid separation, after which solid particles are dried and packaged, while the remaining saturated effluent solution is pressurized and then recycled into the guide bucket.

2. The process of claim 1, wherein the water content of the cyclohexane oxidation solution after mixing thoroughly with water in step (b) is 0.5%-0.8% by volume.

3. The process of claim 1, wherein the second separation step is carried out at a temperature of 60-130° C. and a pressure drop of 0.15 MPa.

4. The process of claim 1, wherein the third separation step is carried out at a temperature of 60-90° C. and a pressure drop of 0.08 MPa.

5. The process of claim 1, wherein the third separation step is carried out with a gravity sedimentation tank.

6. An apparatus for separating and recovering waste alkali liquor from a cyclohexane oxidation solution, comprising:
a saponification separator, used for sedimentating by gravity a cyclohexane oxidation solution that contains a solution of sodium hydroxide, giving a mixture from a first separation step including a cyclohexane oxidation solution removed of over 99% alkali liquor;
a first mixer connected to the saponification separator, used for infusing water into the mixture from the first separation step and mixing thoroughly the mixture from the first separation step with water;
a first water-washing separator connected to the first mixer, used for washing the mixture from the first separation step with water, so that alkaline species in the mixture migrate to water and the alkaline species in water are enriched, wherein the resulting mixture of the mixture from the first separation step and water which are mixed thoroughly is subjected to gravity sedimentation to obtain a mixture from a second separation step including a cyclohexane oxidation solution further removed of 95%-99% alkali liquor;

a second mixer connected to the first water-washing separator, used for infusing water into the mixture from the second separation step and mixing thoroughly the mixture from the second separation step with water;

a second water-washing separator connected to the second mixer, used for washing the mixture of the second separation step with water, wherein the resulting mixture of the mixture from the second separation step and water which are mixed thoroughly is subjected to gravity sedimentation to obtain a mixture from a third separation step including a cyclohexane oxidation solution further removed of 95%-99% alkali liquor;

a vortex separator connected to the second water-washing separator, used for vortex-separating the mixture from the third separation step at a temperature in the range of 50-200° C. and a pressure drop in the range of 0.1-0.25 MPa to further remove alkali liquor comprising alkaline species, giving a mixture from a fourth separation step including a cyclohexane oxidation solution further removed of 85%-98% alkali liquor; the vortex separator comprising a tank body, an inlet for supplying the cyclohexane oxidation solution further removed of 95%-99% alkali liquor from the second water-washing separator, an outlet for discharging alkali liquor comprising alkaline species, and an outlet for discharging the cyclohexane oxidation solution further removed of 85%-98% alkali liquor, wherein the inlet for supplying the cyclohexane oxidation solution further removed of 95%-99% alkali liquor from the second water-washing separator and the outlet of the second water-washing separator for discharging the cyclohexane oxidation solution further removed of 95%-99% alkali liquor are connected via a pipe;

a coalescence separator connected to the vortex separator, used for coalescence-separating the mixture of the fourth separation step at a temperature in the range of 50-200° C. and a pressure drop in the range of 0.05-0.15 MPa to further remove alkali liquor comprising alkaline species, giving a cyclohexane oxidation solution comprising less than 3 mg/L $Na^+$ that is left over; the coalescence separator comprising a tank body, an inlet for supplying the cyclohexane oxidation solution removed of 85%-98% alkali liquor from the vortex separator, an outlet for discharging alkali liquor comprising alkaline species, and an outlet for discharging the cyclohexane oxidation solution comprising less than 3 mg/L $Na^+$ that is left over, wherein the inlet for supplying the cyclohexane oxidation solution further removed of 85%-98% alkali liquor from the vortex separator and the outlet of the vortex separator for discharging the cyclohexane oxidation solution further removed of 85%-98% alkali liquor are connected via a pipe;

an incinerator disposed underneath the saponification separator, the first water-washing separator, the second water-washing separator, the vortex separator and the coalescence separator, for incinerating the removed alkali liquor to obtain a molten effluent;

a guide bucket disposed underneath the outlet of the incinerator for the molten effluent to flow out, used for keeping a saturated solution of sodium carbonate spurting to form a saturated effluent solution and for recycling the saturated effluent solution;

a spurting nozzle for a gas-water mixture disposed underneath the outlet of the incinerator for the molten effluent to flow out, used for crushing the molten effluent; and a solid-liquid separator connected to the guide bucket in circulation, used for subjecting the saturated effluent solution comprising solids to a solid-liquid separation, wherein the second water-washing separator includes a gravity sedimentation tank that comprises a tank body, an inlet for supplying the mixture from the second mixer, an outlet for discharging alkali liquor comprising alkaline species, and an outlet for discharging the mixture from the third separation step including the cyclohexane oxidation solution removed of 95%-99% alkali liquor.

7. The apparatus of claim 6, wherein a water phase flux in the vortex separator is 1%-5% that of an entrance flux therein.

* * * * *